(12) United States Patent
Hopkinson et al.

(10) Patent No.: US 8,278,245 B2
(45) Date of Patent: Oct. 2, 2012

(54) CORROSION INHIBITORS FOR AQUEOUS PESTICIDE FORMULATIONS

(75) Inventors: Michael Hopkinson, Greensboro, NC (US); Giulia Capuzzi, Greensboro, NC (US); Sarah Cush, Greensboro, NC (US); Carolyn Moore, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 106 days.

(21) Appl. No.: 10/580,062

(22) PCT Filed: Nov. 19, 2004

(86) PCT No.: PCT/US2004/038945
§ 371 (c)(1),
(2), (4) Date: Feb. 12, 2007

(87) PCT Pub. No.: WO2005/060492
PCT Pub. Date: Jul. 7, 2005

(65) Prior Publication Data
US 2008/0039329 A1 Feb. 14, 2008

Related U.S. Application Data

(60) Provisional application No. 60/527,555, filed on Dec. 5, 2003.

(51) Int. Cl.
*A01N 25/00* (2006.01)
*A01N 25/02* (2006.01)
*A01N 25/04* (2006.01)
(52) U.S. Cl. .................................................. 504/116.1
(58) Field of Classification Search ................ 504/116.1
See application file for complete search history.

(56) References Cited

U.S. PATENT DOCUMENTS

| | | | | |
|---|---|---|---|---|
| 4,331,490 | A * | 5/1982 | Palgrave et al. | 149/46 |
| 5,416,061 | A | 5/1995 | Hewett et al. | |
| 5,620,678 | A * | 4/1997 | Burke | 424/45 |
| 5,704,961 | A * | 1/1998 | Hudson | 71/30 |
| 6,890,889 | B1 * | 5/2005 | Wichert et al. | 504/348 |
| 6,924,250 | B2 * | 8/2005 | Cornes | 504/136 |
| 2001/0051591 | A1 * | 12/2001 | Ferrett et al. | 504/103 |
| 2005/0202972 | A1 * | 9/2005 | Piper et al. | 504/190 |

* cited by examiner

*Primary Examiner* — Fereydoun G Sajjadi
*Assistant Examiner* — Courtney Brown
(74) *Attorney, Agent, or Firm* — James Cueva

(57) ABSTRACT

The present invention relates to aqueous-containing pesticide concentrates containing an ionic nitrate salt additive as a corrosion inhibitor as well as pesticide compositions prepared from these concentrates and to the use of said compositions for controlling pests.

20 Claims, No Drawings

CORROSION INHIBITORS FOR AQUEOUS PESTICIDE FORMULATIONS

This application is a 371 of International Application No. PCT/US2004/038945 filed Nov. 19, 2004, which claims priority to U.S. 60/527,555 filed Dec. 5, 2003, the contents of which are incorporated herein by reference.

The present invention relates to pesticidal concentrates comprising at least one pesticide and an ionic nitrate salt. The present invention also relates to pesticide compositions prepared from these concentrates and to the use of said compositions for controlling pests.

BACKGROUND OF THE INVENTION

Aqueous-based pesticide formulations are increasingly popular due to their improved profile for mammalian toxicity and ecological effects, as well as reduced costs, compared to formulations utilizing an organic solvent as diluent. Unfortunately, introduction of even a small amount of water into a pesticide composition increases the potential for corrosion of metal surfaces of equipment used in manufacturing, storage, transportation or packaging of the product These corrosion characteristics may result in increased equipment maintenance costs or equipment failure.

The use of additives to reduce corrosion in pesticide compositions is known in the art However, the additives and applications disclosed are very specific in nature. For example, U.S. Pat. No. 2,788,307 discloses use of $Na_2S_2O_3$ to reduce tinplate corrosion in contact with solvent-based lindane or DDT formulations. U.S. Pat. No. 2,630,380 discloses aryloxy polyethylene glycol compounds as inhibitors of corrosion in formulations based on 2,4-dinitro-6-alkylphenols. Use of bis(m-methylphenyl)phosphate to prevent iron corrosion in the presence of S-methyl-N-[(methylcarbamoyl)oxy] thioacetimidate is disclosed in JP 56034562. JP 2000034201 discloses compositions containing silica for preventing corrosion of containers by aqueous aerosols of pyrethroid insecticides. U.S. Pat. No. 5,061,698 discloses compositions based on boric acid with utility as corrosion inhibitors. U.S. Pat. No. 5,032,318 discloses $C_{13}$-$C_{14}$ alkylamine salts of N-acylsarcosine as corrosion inhibitiors for aerosols in tinplated steel cans. U.S. Pat. No. 5,118,444 discloses use of a specific class of amine oxides to reduce corrosion in aqueous pesticide compositions. The potential for corrosion in aqueous-based formulations is increased when the formulation is acidic in pH. There are a number of important pesticide active ingredients that contain an acid moiety in their structure and an aqueous-based formulation of these products may have an acidic pH. There may be other reasons for the pH of a pesticide formulation to be maintained at an acidic level, such as improved chemical stability for the active ingredient or improved physical stability for the product on storage. The presence of dissolved salts such as ionic chlorides or pesticide active ingredients present in salt or metal complex form may also accelerate corrosion of metal surfaces.

Surprisingly, it has been found that certain nitrate salt additives significantly reduce the corrosion properties of aqueous-based pesticide formulations, even with acidic pH levels and in the presence of a salt.

The additives of the present invention may be incorporated in the aqueous pesticide composition during the initial formulation process or may be added at any subsequent stage of storage, transportation or packaging to reduce corrosion. The additives of the present invention have the further advantage of being readily available at relatively low cost.

The use of nitrate salts, especially ammonium nitrate, as nitrogen fertilizer is long established in the agricultural industry, and the use of ammonium nitrate or other nitrogen fertilizer solutions as a tank mix carrier liquid for application of herbicides is frequently included on the label instructions for the product. However, the use of nitrate salts in nitrogen fertilizer carrier liquids involves large quantities per acre.

There are also reports in the patent literature (U.S. Pat. No. 5,658,855, US 2003104947, US 2003125211 and WO 02/19823) for use of compositions containing ammonium nitrate as application spray additives for increased herbicide activity. However, the pesticide compositions that incorporate these additives are very dilute spray mixtures that are typically prepared just prior to use by mixing components directly in the spray equipment.

SUMMARY OF THE INVENTION

There are now provided certain corrosion inhibitor additives for aqueous-containing pesticide formulations that will be effective under potentially severe corrosion conditions. The compositions of the present invention have particular utility when the pH of the composition is less than or equal to 6 and/or wherein a salt or metal complex is present, either as the pesticide active ingredient or as a formulation auxiliary.

In one embodiment, the invention relates to a pesticide concentrate comprising:
a) water
b) at least one pesticide
c) an amount of an ionic nitrate salt additive that is effective in reducing corrosion of metal surfaces
d) optionally, other formulation auxiliaries
wherein the ratio of component c) to component b) is less than or equal to 0.3:1.

The invention also relates to pesticide compositions prepared from these concentrates and to the use of said compositions for controlling pests.

DETAILED DESCRIPTION OF THE INVENTION

It has surprisingly been found that pesticidal concentrates having reduced corrosion properties can be obtained by incorporating into said concentrate an ionic nitrate salt.

The invention relates to a pesticide concentrate comprising:
a) 2-85% by weight water
b) 5-90% by weight of at least one pesticide
c) an ionic nitrate salt additive in an amount effective in reducing corrosion of metal surfaces
d) optionally, other formulation auxiliaries.
wherein the ratio of component c) to component b) is less than or equal to 0.3:1.

The invention also relates to pesticide compositions prepared from these concentrates, to the use of said ionic nitrate salt additives in reducing corrosion of metal surfaces and to the use of said compositions for controlling pests comprising the step of applying to the locus in need of protection an effective amount of the inventive pesticide composition.

The compositions of the present invention have particular utility when the pH of the composition is less than or equal to 6 and/or wherein a salt or metal complex is present, either as the pesticide active ingredient or as a formulation auxiliary.

Nitrate salts suitable for use as corrosion inhibitor additives in the present invention include ammonium nitrate, alkali metal nitrates and alkaline earth metal nitrates, for example sodium nitrate and calcium nitrate. These salts are readily commercially available. The additives of the present invention may be incorporated in the pesticide composition during the initial formulation process or may be added at any subsequent stage of storage, transportation or packaging to reduce corrosion.

The concentrates of the present invention contain water in a range of 2% to 85% by weight, preferably 5% to 65% by weight. The pesticide concentration ranges from 5% to 90% by weight, preferably 25% to 75% by weight, with the nitrate salt additive present in an amount effective in reducing corrosion of metal surfaces, typically in a concentration ranging from 0.001% to 10% by weight The ratio of nitrate salt additive to pesticide concentration is less than or equal to 0.3:1.

A preferred embodiment of the invention is a composition comprising ammonium nitrate as the corrosion inhibitor additive.

An additional preferred embodiment of the invention is use of an ionic nitrate salt additive in an aqueous pesticide composition for corrosion inhibition.

Pesticide active ingredients suitable for the present invention include both water-soluble and water-insoluble compounds. Water-soluble active ingredients include pesticides or plant growth regulators such as acephate, acifluorfen, acrolein, amitrole, asulam, benazolin, bentazon, bialaphos, borax, bromacil, bromoxynil, butoxycarboxim, calcium polysulfide, cartap, chloramben, chlormequat, chloroacetic acid, chlorphonium, clofencet, clopyralid, cloxyfonac, copper sulfate, cyanamide, 2,4-D, 2,4-DB, dalapon, daminozide, dicamba, dichlorprop, diclofop, dicrotophos, difenzoquat, dikegulac, diquat, endothall, ethephon, fenac, fenoxaprop, flamprop, fluazifop, fluoroglycofen, flupropanate, fomesafen, formetanate, fosamine, fosetyl, glufosinate, glyphosate, guazatine, haloxyfop, hydroxyquinoline sulfate, imazameth, imazamethabenz, imazamox, imazapic, imazapyr, imazaquin, imazethapyr, iminoctadine, ioxynil, kasugamycin, MCPA, MCPB, mecoprop, mepiquat, mercuric chloride, metam, methamidophos, methomyl, methylarsonic acid, mevinphos, monocrotophos, nabam, naptalam, nicotine, nitenpyram, nonanoic acid, omethoate, oxamyl, oxydemeton-methyl, paraquat, phosphamidon, picloram, polyoxin B, propamocarb, sulfamic acid, 2,3,6-TBA, thiocyclam, trichlorfon, trichloroacetic acid, triclopyr, validamycin and vamidothion, as well as agriculturally acceptable salts and esters thereof.

Preferred water-soluble active ingredients include glyphosate, glufosinate, paraquat, diquat, dicamba, fomesafen, 2,4-D, 2,4-DB and agriculturally acceptable salts thereof.

Most preferred water-soluble active ingredients include glyphosate, glufosinate, paraquat and agriculturally acceptable salts and esters thereof. Preferred salts for glyphosate include isopropylammonium, potassium, ammonium and trimethylsulfonium.

Water-insoluble active ingredients include pesticides, herbicide antidotes or plant growth regulators such as abamectin, acetochlor, aclonifen, acrinathrin, amitraz, atrazine, azadirachtin, azamethiphos, azinphos-methyl, azocyclotin, azoxystrobin, BAS 670, benalaxyl, benomyl, benoxacor, bensulfuron-methyl, bensultap, benzofenap, 6-benzylaminopurine, bifenox, bifenthrin, bitertanol, bromobutide, bromofenoxim, bromopropylate, bromuconazole, buprofezin, butafenacil, captafol, captan, carbendazim, chinomethionat, chlomethoxyfen, chlorbromuron, chlorfenapyr, chlorfenson, chlorfluazuron, chlorimuron-ethyl, chlomitrofen, chlorothalonil, chlorotoluron, chlorthal-dimethyl, chlozolinate, clofentezene, clomeprop, coumaphos, cyanilide, cyfluthrin, beta-cyfluthrin, cypermethrin, alpha-cypermethrin, theta-cypermethrin, cyometrinil, cyprodinil, daimuron, DDT, deltamethrin, desmedipham, diafenthiuron, dichlobenil, dichlofluanid, dichlormid, 4-dichloroacetyl-1-oxa4-aza-spiro[4,5] decane, dichlorofen, diclomezine, dicloran, dicofol, dicyclonon, diethofencarb, diflubenzuron, diflufenican, dimefuiron, dimethenamide, dimethomorph, diniconazole, dinitramine, dithianon, diuron, endosulfan, epoxiconazole, esfenvalerate, ethametsulfuron-methyl, etoxazole, famoxadone, fenarimol, fenazaquin, fenbuconazole, fenbutatin oxide, fenclorim, fenfuram, fenoxaprop-ethyl, fenoxycarb, fenpiclonil, fenpyroximate, fentin, fipronil, flamprop-methyl, flazasulfuron, flurazole, fluazinam, fluazuron, flucycloxuron, fludioxonil, flufenoxuron, flumetralin, flumetsulam, flumiclorac-pentyl, flumioxazin, fluoroimide, flupoxam, fluquinconazole, fluridone, flurtamone, flusulfamide, flutolanil, fluxofenim, folpet, forchlorfenuron, furilazole, glyphosate acid, halofenozide, gamma-HCH, hexachlorobenzene, hexaconazole, hexaflumuron, hexythiazox, hydramethylnon, imibenconazole, inabenfide, ipconazole, iprodione, isoproturon, isoxaben, isoxaflutole, isoxapyrifop, kresoxim-methyl, lactofen, lenacil, linuron, lufenuron, mancozeb, maneb, mefenacet, mepanipyrim, mepronil, mesotrione, mesotrione metal complexes, metalaxyl, metconazole, methabenzthiazuron, methiocarb, metolachlor, s-metolachlor, methoxychlor, metiram, metobenzuron, milbemectin, 2-(1-naphthyl)acetamide, naproanilide, neburon, nickel bis(dimethyldithiocarbamate), nicosulfuron, norflurazon, novaluron, nuarimol, oryzalin, oxabetrinil, oxadiazon, oxine copper, oxolinic acid, oxyfluorfen, paclobutrazol, pencycuron, pentachlorophenol, phenmedipham, N-phenylphthalamic acid, phthalide, primisulfuron, procymidone, prodiamine, prometryn, propazine, propiconazole, propineb, propyzamide, propsulfuron, pyrazolynate, pyrazosulfuron-ethyl, pyributicarb, pyridaben, quinclorac, quintozene, quizalofop-ethyl, resmethrin, rimsulfuron, rotenone, siduron, simazine, sulcotrione, sulfluramid, sulfur, tebuconazole, tebufenozide, tebufenpyrad, tebupirimfos, tecloftalam, tecnazene, teflubenzuron, terbuthylazine, terbutryn, tetrachlorvinphos, tetradifon, tetramethrin, thiamethoxam, thiazopyr, thidiazuron, thifluzamide, thiodicarb, thiophanate-methyl, thiram, tolclofos-methyl, tolylfluanid, tralkoxydim, tralomethrin, triadimefon, triadimenol, triazoxide, trietazine, triflumuron, triforine, trimethacarb, triticonazole, uniconazole, vinclozolin, zineb and ziram as well as agriculturally acceptable salts and esters thereof Preferred water-insoluble active ingredients include mesotrione, and mesotrione metal chelates, atrazine, simazine, terbuthylazine, sulcotrione, metolachlor, s-metolachlor, acetochlor, dimethenamide, abamectin, thiamethoxam, azoxystrobin, metalaxyl, propiconazole, benoxacor, dichlormid, 4-dichloroacetyl-1-oxa4-aza-spiro[4,5] decane, and furilazole.

Most preferred water-insoluble active ingredients include mesotrione, and mesotrione metal chelates, atrazine, metolachlor, s-metolachlor, and benoxacor. Preferred mesotrione metal chelates include those wherein the metal is a transition metal selected from the group of copper, cobalt, zinc and nickel.

In a particularly preferred embodiment, the compositions comprise a metal chelate of mesotrione, preferably a copper or zinc chelate of mesotrione.

Formulation auxiliaries that may be present in the form of salts include alkali metal and alkaline earth metal chlorides, such as sodium chloride and calcium chloride.

Formulation auxiliaries for the present invention further include, but are not limited to, surface-active agents, thixotropic agents, antifoaming agents, antifreezing agents and preservatives.

Typically, surfactants will be present in the concentrates of the invention. Suitable surface-active compounds are, depending on the nature of the active ingredient, non-ionic, cationic and/or anionic surfactants and mixtures of surfactants having good emulsifying, dispersing and wetting properties. Examples of suitable anionic, non-ionic and cationic surfactants are listed, for example, in U.S. Pat. No. 6,063,732 column 5, line 1 to column 6, line 2, the contents of which are incorporated herein by reference.

Furthermore, the surfactants customarily employed in formulation technology, which are described, inter alia, in "Mc Cutcheon's Detergents and Emulsifiers Annual" MC Publishing Corp., Ridgewood N.J., 1981, Stache, H., "Tensid-Taschenbuch", Carl Hanser Verlag, MunichNienna, 1981 and M. and J. Ash, "Encyclopedia of Surfactants", Vol I-III, Chemical Publishing Co., New York, 1980-81, are also suitable for preparation of the herbicidal compositions according to the invention.

The amount of surfactant(s) depends on the particular active ingredients selected for the composition and the absolute and relative amounts of these desired. Suitable amounts of stabilizing system components selected from the classes or specific examples provided herein can be determined by routine experimentation, the test being that substantially no phase separation, sedimentation or flocculation is exhibited by the composition following storage at 20-25° C. for a period of 24 hours, or, for preferred embodiments, following a longer period of storage over a broader range of temperatures as indicated above. Typically the total concentration of all surfactants in the composition as a whole is about 1% to about 30% by weight, excluding the weight of counterions, if present.

The invention relates also to pesticide compositions obtained by i) diluting the pesticide concentrate of the present invention in a suitable carrier, such as water, such that the final concentration of the pesticide is between about 0.01% and about 10% of active ingredient (a.i.).

The invention relates also to a method for the control of pests, said method comprising forming a pesticide composition by i) diluting the pesticide concentrate of the present invention in a suitable carrier, such as water, such that the final concentration of the pesticide is between about 0.01% and about 10% of active ingredient (a.i.) and ii) treating the desired area, such as crop, their seeds or seedlings or the crop area, with said composition.

The invention relates also to the use of an ionic nitrate salt additive in an aqueous pesticide composition for corrosion inhibition.

The composition according to the invention is suitable for all methods of application conventionally used in agriculture, e.g. pre-emergence application, post-emergence application and seed dressing.

The composition according to the invention is suitable especially for controlling pests in crops of useful plants, such as cereals, rape, sugar beet, sugar cane, plantation crops, rice, maize and soybeans. "Crops" are to be understood also to include those crops that have been made tolerant to pests and pesticides, including herbicides or classes of herbicides, as a result of conventional methods of breeding or genetic engineering. The components used in the composition of the invention can be applied in a variety of ways known to those skilled in the art, at various concentrations. The rate at which the pesticidal compositions are applied will depend upon the particular type of pest to be controlled, the degree of control required, and the timing and method of application.

Crop areas are areas of land on which the cultivated plants are already growing or in which the seeds of those cultivated plants have been sown, and also areas of land on which it is intended to grow those cultivated plants.

Other active ingredients such as co-herbicides, fungicides, insecticides, acaricides and nematicides may be present in the emulsifiable concentrate or may be added as a tank-mix partner with the emulsifiable concentrate.

Suitable thixotropic additives are compounds that impart a pseudoplastic flow behavior to the formulation, i.e. a high viscosity in the resting state and a low viscosity in the agitated state. Examples of suitable compounds include polysaccharides such as xanthan gum, Kelzan® by Kelco or Rhodopol® 23 by Rhone Poulenc.

Suitable antifoams include, for example, silicone emulsions, long-chain alcohols, fatty acids, organofluorine compounds and mixtures of these.

The following examples illustrate further some of the aspects of the invention but are not intended to limit its scope. Where not otherwise specified throughout this specification and claims, temperatures are given in degrees centigrade and percentages are by weight.

Example 1

Preparation of Mesotrione Copper Suspension Concentrate Test Material

The test material is prepared according to the following composition:

| | |
|---|---|
| Mesotrione | 35.0% |
| Soprophor BSU surfactant (tristyrylphenol 16 mole ethoxylate) | 3.5% |
| Acetic acid (glacial) | 6.2% |
| Copper hydroxide (100%) | 5.1% |
| Silicone antifoaming agent | 0.1% |
| Xanthan gum thixitropic agent | 0.1% |
| Water | 50.0% |

Mix the water, acetic acid and copper hydroxide. Add the mesotrione followed by the surfactant, antifoam and thixotropic agent and mix until uniform. Mill until the particle size of the suspended solid is below 10 microns. The resulting mixture has a pH around 3.0.

Example 2

Testing of Corrosion Inhibitor Additive Candidates

The following procedure was used to test a series of 17 candidate corrosion inhibitor materials along with a control sample containing no inhibitor.
Weigh into a 16 ounce sample jar and mix thoroughly:
 1) 325 grams of the mesotrione copper suspension concentrate from Example 1,
 2) 15 grams of xanthan gum thixitropic agent/water mixture (2% concentration), and
 3) 10 grams of a candidate corrosion inhibitor material.

Immerse two weighed 304 stainless steel corrosion coupons (one with weld and another without weld) in the liquid, close and seal the lid, and place the jar in an oven maintained at 50° C. After four weeks of storage at 50° C., remove the coupon from the liquid, wash with a firm toothbrush in soap and water, rinse with acetone and dry. Weigh the coupon and visually inspect to determine the severity of corrosion.

Results of the corrosion inhibition tests are presented in Table 1 below.

TABLE 1

Corrosion Inhibition Results

| Sample Code | Additive | Weight Loss of Welded | Weight Loss of Flat | Initial pH |
|---|---|---|---|---|
| 1 | Control | −0.0060 | −0.0138 | 3.0 |
| 2 | Alkasperse 752 | −0.2356 | −0.0202 | 3.0 |
| 3 | EDTA tetra Na Salt | −0.0042 | −0.0069 | 4.0 |
| 4 | C8 amine 5EO | −0.0161 | −0.0307 | 3.6 |
| 5 | Agent S32/A | −0.0066 | −0.0275 | 3.1 |
| 6 | Sodium Molybdate | −0.0019 | −0.0163 | 4.1 |
| 7 | Witcamine TAM-45 | −0.0131 | −0.2064 | 3.4 |
| 8 | Surfynol 61 | −0.0173 | −0.0152 | 3.0 |
| 9 | Surfynol 104 | −0.0231 | −0.0255 | 3.0 |
| 10 | Tetronic 1107 | −0.0345 | −0.0263 | 3.1 |
| 11 | Boric Acid | −0.0231 | −0.0369 | 3.0 |
| 12 | Agrimer VEMA ES33 Neut. | −0.0142 | −0.0071 | 3.2 |
| 13 | Tetronic 304 | −0.0142 | −0.0199 | 3.3 |
| 14 | Agent 2669-29 | −0.0151 | −0.0178 | 2.8 |
| 15 | Ammonyx Cetac 30 | −0.0178 | −0.0207 | 2.9 |
| 16 | Agent 2668-98 | −0.0109 | −0.0229 | 3.0 |
| 17 | Genamin C100 | −0.0131 | −0.0248 | 3.3 |
| 18* | Ammonium nitrate | −0.0005 | −0.0005 | 3.0 |

*Composition within the scope of the present invention

The control sample (#1) that had no corrosion inhibitor present showed significant corrosion of the 304 stainless steel coupon as indicated by the weight loss of both the welded and flat coupons and visual inspection that showed heavy rust present. Many of the candidate inhibitors actually resulted in increased corrosion while several others showed moderate corrosion inhibition. Two samples (#6, #7) showed weight increases, probably due to plating of copper on the coupons. The ammonium nitrate sample (#18) of the present invention, however, showed a dramatic decrease in corrosion vs. the control as evidenced by a very small weight loss for both coupons and visual inspection that showed no rust or other residue present.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. A pesticide concentrate comprising:
a) 2-85% by weight water;
b) 5-90% by weight of at least one pesticide comprising mesotrione, an agriculturally acceptable salt of mesotrione or a metal chelate of mesotrione;
c) an amount of an ionic nitrate salt additive effective in reducing corrosion of metal surfaces, said ionic nitrate salt additive comprising ammonium nitrate; and
d) optionally, other formulation auxiliaries;
wherein the ratio of component c) to component b) is less than or equal to 0.3:1.

2. The concentrate of claim 1 wherein the pH of the composition is 6 or less.

3. The concentrate of claim 1 wherein the at least one pesticide is in the form of a salt of mesotrione or a metal chelate of mesotrione.

4. The concentrate of claim 1 comprising at least one formulation auxiliary in the form of a salt.

5. The concentrate of claim 4 wherein the formulation auxiliary in the form of a salt comprises at least one alkali metal or alkaline earth metal chloride.

6. The concentrate of claim 1 wherein the at least one pesticide comprises a copper or zinc chelate of mesotrione.

7. A pesticidal composition obtained by diluting a concentrate according to claim 1 into a suitable amount of carrier.

8. A pesticidal composition according to claim 7 wherein the carrier is water.

9. The pesticidal composition of claim 7 further comprising at least one member selected from the group consisting of herbicides, fungicides, insecticides, acaricides, and nematicides.

10. A method for the selective control of pests in crops of useful plants, which method comprises treating the useful plants, their seeds or seedlings or the crop area thereof with a pesticidal composition according to claim 7.

11. The concentrate of claim 1 wherein the pesticide concentrate comprises from 0.001 to 10 wt % of the ionic nitrate salt additive.

12. A pesticide concentrate comprising:
a) 2-85% by weight water;
b) 5-90% by weight of at least one pesticide comprising mesotrione, an agriculturally acceptable salt of mesotrione or a metal chelate of mesotrione;
c) an amount of an ionic nitrate salt additive effective in reducing corrosion of metal surfaces, said ionic nitrate salt additive comprising ammonium nitrate; and
d) one or more other formulation auxiliaries;
wherein the ratio of component c) to component b) is less than or equal to 0.3:1.

13. The concentrate of claim 12 wherein the at least one pesticide comprises a copper or zinc chelate of mesotrione.

14. The concentrate of claim 12 wherein the pH of the composition is 6 or less.

15. The concentrate of claim 12 wherein the pesticide concentrate comprises from 0.001 to 10 wt % of the ionic nitrate salt additive.

16. A pesticidal composition obtained by diluting a concentrate according to claim 12 into a suitable amount of carrier.

17. A pesticide concentrate comprising:
a) 2-85% by weight water;
b) 5-90% by weight of at least one pesticide comprising a copper or zinc chelate of mesotrione;
c) 0.001 to 10 wt % of an ionic nitrate salt additive effective in reducing corrosion of metal surfaces, said ionic nitrate salt additive comprising ammonium nitrate; and
d) optionally, other formulation auxiliaries;
wherein the ratio of component c) to component b) is less than or equal to 0.3:1.

18. A pesticidal composition obtained by diluting a concentrate according to claim 17 into a suitable amount of carrier.

19. The concentrate of claim 12 wherein said one or more other formulation auxiliaries comprise an alkali metal salt, an alkaline earth metal chloride, a surfactant, a thixotropic agent, an antifoaming agent, an antifreezing agent, a preservative, or any combination thereof.

20. The concentrate of claim 12 wherein said one or more other formulation auxiliaries comprise a surfactant, a thixotropic agent, and an antifoaming agent.

* * * * *